United States Patent
Adorante (12)

(10) Patent No.: US 6,326,389 B1
(45) Date of Patent: *Dec. 4, 2001

(54) INHIBITION OF NONINACTIVATING NA CHANNELS OF MAMMALIAN OPTIC NERVE AS A MEANS OF PREVENTING OPTIC NERVE DEGENERATION ASSOCIATED WITH GLAUCOMA

(75) Inventor: Joseph S. Adorante, Irvine, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/273,832

(22) Filed: Mar. 22, 1999

Related U.S. Application Data

(63) Continuation-in-part of application No. 08/827,194, filed on Mar. 27, 1997, now Pat. No. 5,922,746.

(51) Int. Cl.$^7$ .................................................. A61K 31/425
(52) U.S. Cl. .......................................... 514/373; 514/912
(58) Field of Search ..................................... 514/373, 912

(56) References Cited

U.S. PATENT DOCUMENTS 5,624,945 * 4/1997 Bousseau et al. .................... 514/367

\* cited by examiner

Primary Examiner—Zohreh Fay
(74) Attorney, Agent, or Firm—Walter A. Hackler

(57) ABSTRACT

A method an composition for altering a plausible sequence of pathological events in retinal ganglion cells associated with glaucoma, the sequence including membrane depolarization, influx of millimolar amounts of $Na^+$ via non-inactivating $Na^+$ channels, and the lethal elevation of cell $Ca^{2+}$ due to reversal of the $Na^+/Ca^{2+}$ exchanger. The method includes blocking, by administration of a selected composition, of associated, non-inactivating $Na^+$ channels in retinal ganglion cells in order to limit $Na^+/Ca^{30}$ exchange in the retinal ganglion cells and prevent buildup of the $Ca^{2+}$ level in the retinal ganglion cells to a lethal level. The results in a method of preventing retinal ganglion cell death, associated with glaucoma, by administering to the optic nerve of a mammal, a compound which blocks the non-inactivating sodium ion channels of the optic nerve. Alternately, said invention relates to a method of preventing optic retinal ganglion cell death in a human by administering to the retinal ganglion cells of said human a compound which blocks the non-inactivating sodium ion channel of the retinal ganglion cells.

4 Claims, 2 Drawing Sheets

Normal Conditions
Membrane Potential= -75 mV

Ischemic Conditions
Membrane Potential depolarized

INHIBITION OF NONINACTIVATING NA CHANNELS OF MAMMALIAN OPTIC NERVE AS A MEANS OF PREVENTING OPTIC NERVE DEGENERATION ASSOCIATED WITH GLAUCOMA

The present application is a continuation-in-part of U.S. Ser. No. 08/827,194, filed on Mar. 27, 1997 now U.S. Pat. No. 5,992,746.

BACKGROUND OF INVENTION

1. Field of the Invention

The present invention relates to a method of preventing retinal ganglion cell death, associated with glaucoma, by administering to retinal ganglion cells of a mammal, a compound which blocks the putative non-inactivating sodium ion channels of the above cell type.

2. Brief Description of the Art

Glaucoma is an optic neuropathy associated with elevated intraocular pressures which are too high for normal function of the eye, and results in irreversible loss of visual function. (See for example, Dreyer et al "Elevated glutamate levels in the vitreous body of human and monkeys with glaucoma", Arch. Ophthalmology 114:299-305, 1996) It is estimated in medical science that glaucoma afflicts approximately 2 per cent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma.

Primary open angle glaucoma (POAG) is associated with a rise in intraocular pressure (IOP). This increase in IOP is believed to contribute to the loss of optic nerve function which ultimately leads to blindness. Reduction of IOP is therefore a crucial component in the management of POAG. However, in many individuals lowering of IOP is not sufficient or ineffective in preventing vision loss associated with POAG.

It is thought that a novel class of sodium channels residing within the optic nerve of the rat are responsible for damage to the rat optic nerve following anoxia or hypoxia. However, in glaucoma the sequence of pathological events leading to the loss of optic nerve function, is not known.

The drugs currently utilized in the treatment of glaucoma include miotics (e.g., pilocarpine, carbachol, and acetylcholinesterase inhibitors), sympathomimetrics (e.g., epinephrine and dipivalylepinephrine), beta-blockers (e.g., betaxolol, levobunolol and timolol), alpha-2 agonists (e.g., para-amino clonidine) and carbonic anhydrase inhibitors (e.g., acetazolamide, methazolamide and ethoxzolamide). Miotics and sympathomimetics are believed to lower intraocular pressure by increasing the outflow of aqueous humor, while beta-blockers, alpha-2 agonists and carbonic anhydrase inhibitors are believed to lower intraocular pressure by decreasing the formation of aqueous humor. All five types of drugs have potential side effects. Miotics, such as pilocarpine, can cause blurring of vision and other visual side effects which may either decrease patient compliance or require termination of miotic drug therapy. Carbonic anhydrase inhibitors can also cause serious side effects which affect patient compliance and/or necessitate withdrawal of the drug therapy. At least one beta-blocker, timolol, has increasingly become associated with serious pulmonary side effects attributable to its effect on beta-2 receptors in pulmonary tissue.

As a result additional antiglaucoma drugs are being developed, e.g., prostaglandin derivatives, muscarinic antagonists, etc. However, none of the above drugs are designed to directly interact with the retinal ganglion cell and its associated axon.

Thus, it would be desirable to prevent the loss of ganglion cell body and axon function, which may be associated with glaucoma by a biological mechanism which does not modulate aqueous humor dynamics and therefore intraocular pressure. Moreover, it would be desirable to treat the retinal ganglion cell body and axon of a mammal directly to prevent the destruction thereof by the glaucomatous condition.

SUMMARY OF THE INVENTION

Surprisingly, it has been discovered in accordance with the present invention, that sodium channel blockers which block the non-inactivating sodium ion channel of the optic nerve of a mammal may be effective for preventing the loss of retinal ganglion cells when such sodium channel blockers are administered and applied in a pharmaceutical composition. Accordingly, the present invention relates to a method of preventing loss of retinal ganglion cells and their associated axons (optic nerve) function, associated with glaucoma, by systemically or directly administering to the eye of a mammals an ophthalmic composition which includes an amount of a sodium channel blocker which is effective to block the non-inactivating sodium ion channel of the ganglion cells of said mammal.

More specifically, the present invention is directed to a method for altering a possible sequence of pathological events in retinal ganglion cells that may be associated with glaucomatous optic neuropathy. The sequence includes the pathological depolarization of retinal ganglion cells, an influx of millimolar amounts of sodium via non-inactivating sodium channels and a subsequent reversal of the sodium/calcium exchanger. Reversal of the sodium/calcium exchanger mediated by both membrane depolarization and increased intracellular sodium causes a toxic buildup of intracellular calcium. The method for altering this sequence includes a step of blocking associated non-inactivating sodium channels in retinal ganglion cells in order to prevent reversal of sodium/calcium ion exchange and subsequent buildup of the calcium ion concentration in the retinal ganglion cells to a lethal level.

Specifically, this blocking is achieved by administering to the retinal ganglion cells a pharmaceutical composition having an active ingredient with non-inactivating sodium channel blocking activity.

Specific examples of sodium channel blockers which are used as the active effective ingredients in the ophthalmic compositions of the present invention are described as benzothialzole, phenyl benzothialzole, disopyramide, propafenone, flecainide, lorcainide, aprindine, encainide, GEA-968, azure A, pancuronium, N-methylstrychnine, CNS 1237, BW1003C87, BW619C89, U54494A, PD85639, ralitoline, C1953, lifarizine, zonisamide and riluzole.

The composition may comprise an ophthalmic solution adapted for administration to the eye of a mammal in the form of intracameral injection.

A direct effect on retinal ganglion cells is an important discovery in accordance with the method of the present invention. However, normal electrical excitability of ganglion cells, crucial for vision, will not be compromised.

Further, a pharmaceutical composition provided in accordance with the present invention useful for preventing retinal ganglion cell death associated with glaucoma with the composition comprising with its active ingredient one or more compounds having non-inactivating sodium channel blocking activity.

More specifically, the present invention provides a method for preventing retinal ganglion cell death associated with glaucoma in an animal of the mammalian species, including humans, which includes the step of administering to the retinal ganglion cells of the mammal a pharmaceutical composition which comprises as its active ingredient one or more compounds having non-inactivating sodium channel blocking activity.

BRIEF DESCRIPTION OF THE DRAWINGS

The advantages and features of the present invention would be better understood by the following description when considered in conjunction with the accompanying drawings.

DETAILED DESCRIPTION OF THE INVENTION

Figure 1:
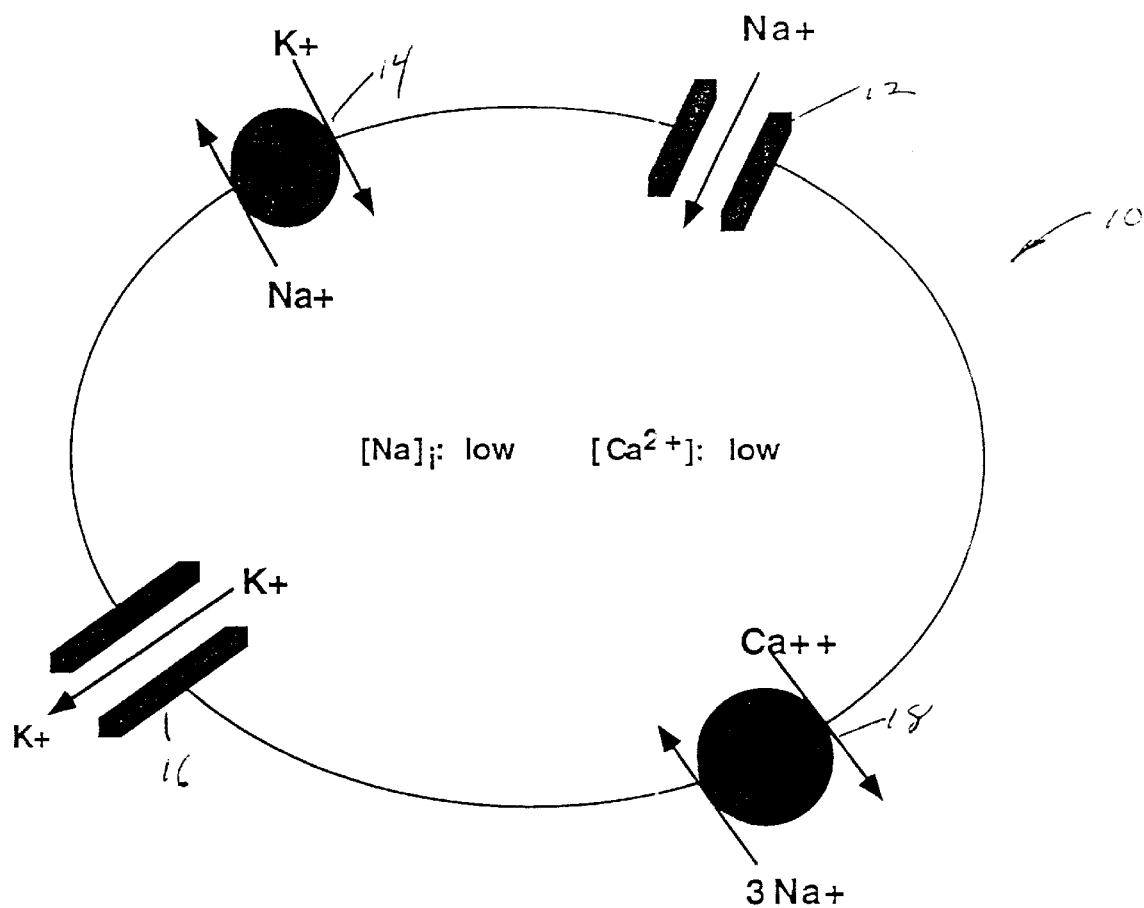
FIG. 1 is a diagram of the assumed relevant transport mechanisms for a retinal ganglion cell under normal conditions.

While not wishing to be bound by theory, it is believed that the death or loss of axons and associated cell bodies comprising the optic nerve is the result of a lethal increase in the intracellular concentration of calcium ion ($Ca^{+2}$) resulting from an influx of sodium ion ($Na^+$) through. a non-inactivating sodium ion channel. While studies have been conducted on rat optic nerve segments (Stys et al, 1995; Waxman, 1995), no application has been made to ganglion cells. There is no expectation of altering a similar sequence of pathological events in retinal cells to prevent death thereof after anoxia based on earlier experiments on rat optic nerves because it is unclear whether (1) a similar sequence of events takes place during glaucoma or (2) whether noninactivating Na channels are present in mammalian retinal ganglion cells, and, if present, the role these channels play in the destruction of retinal ganglion cells that accompanies vision loss associated with glaucoma.

The procedure in rat retinal ganglion cell is as follows:

Following depolarization excitable voltage-dependent Na channels open for about one millisec and then close. Provided the cell membrane remains depolarized, the channels will not reopen until the membrane is repolarized towards its resting state. In contrast to normal excitable Na channels, non-inactivating Na channels can be open at normal resting membrane potentials and can remain open at depolarized potentials. Under pathophysiological conditions such as adenosine triphosphate (ATP) depletion or sustained depolarization Na influx through non-inactivating Na channels can substantially increase intracellular Na. This increase in intracellular Na causes the electrogenic $Na/Ca^{2+}$ exchanger (Ransom et al, 1993; Stys, 1995, Waxman et al, 1992) which normally operates to promote efflux of $Ca^{2+}$ from the cell to reverse operation with a resulting large increase in intracellular $Ca^{+2}$ concentration. The $Ca^{+2}$ concentration of the cell may increase from nanomolar to micromolar levels with the resulting death of said neuronal cell. (Large increases in intracellular $Ca^{+2}$ have been associated with neuronal cell death and prevention of the increase of intracellular $Ca^{+2}$ concentration has been shown to protect neurons of the central nervous system, and rat optic nerve.) In the optic nerve preparation intracellular $Ca^{2+}$ was not measured, however, normal cell $Ca^{2+}$ most cell types including neurons is approximately 100–200 nanomolar. When $Ca^{2+}$ rises to micromolar levels it becomes toxic. Exactly what level of $Ca^{2+}$ in optic nerve triggers cell destruction is not known or at least has not been reported.

Thus, the compounds utilized in accordance with the method of the present invention and in the compositions of the present invention are sodium channel blockers which block the non-inactivating sodium ion channels of the retinal ganglion cells. The sodium channel blockers of the present invention prevent the influx of sodium ions into the neuronal cell through the non-activating sodium channel. Preferably the sodium channel blockers of the present invention will selectively block said non-inactivating sodium channels as opposed to voltage-gated sodium ion channels that inactivate rapidly.

Pharmaceutically acceptable salts of the sodium channel blockers can also be used in accordance with the present invention. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, such as alkali ions, e.g. sodium, potassium, etc. Organic amine salts may be made with amines, particularly ammonium salts such as mono-, di- and trialkyl amines, e.g. alkyl amines wherein each alkyl group may comprise up to six carbon atoms, or ethanol amines. Salts may also be formed with caffeine, tromethamine and similar molecules. It is only important that the cation of any salt of a sodium channel blocker utilized in the compositions or methods of this invention be able to block the non-inactivating sodium channels of the retinal ganglion cell.

For protecting against retinal ganglion cell damage in a mammalian eye, and particularly for prevention of retinal ganglion cell loss in humans exposed to a condition that causes optic neuron loss, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water), saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the optic nerve site of the eye. Preferably, the ophthalmic, therapeutic solutions contain one or more of the active compounds in a concentration range of approximately 0.0001% to approximately 1% (weight by volume) and more preferably approximately 0.0005% to approximately 0.1% (weight by volume).

Any method of administering drugs to the retinal ganglion cell site of a maummalian eye may be employed to administer, in accordance with the present invention, the active compound or compounds to the eye to be treated.

By the term "administering" is meant to include those general systemic drug administration modes, e.g., injection directly into the patient's blood vessels, oral administration and the like, which result in the compound or compounds being systemically available. Also, inter-cameral injection may be utilized to deliver the sodium channel blocker to the retinal ganglion cell site. The primary effect on the mammal resulting from the direct administering of the active compound or compounds to the mammnal's eye is the prevention of optic nerve loss. Preferably, the active useful compound or compounds are applied topically to the eye or are injected directly into the eye.

Injection of ophthalmic preparations, for example ocular drops, gels or creams may be used because of ease of application, ease of dose delivery and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium potassium, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose and hydroxyethyl cellulose.

Tonicity adjustors may be added as needed or convenient. They include, but are not limited to, salts, particularly sodium chloride, potassium chloride, etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Those skilled in the art will recognize that the frequency of administration depends on the precise nature of the active ingredient and its concentration in the ophthalmic formulation.

Specific examples of sodium channel blockers which are used as the active effective ingredients the ophthalmic compositions of the present invention are described as benzothialzole, phenyl benzothialzole, disopyramide, propafenone, flelecainide, lorcainide, aprindine, encainide, GEA-968, azure A, pancuronium, W-methylstrychnine, CNS 1237, BW1003C87, BW619C89, U54494A, PD85639, ralitoline, C1953, lifarizine, zonisamide and riluzole.

A sodium channel blocker, in accordance with the present invention, may be identified by the methods disclosed in "The Extracellular Patch Clamp: A method for Resolving Currents Through Individual Open Channels in Biological membranes",Neher et al Pflugers Archiv V375 pp 219–228 (1978) and "Improved Patch-Clamp Techniques for High-Resolution Current Recording from Cells and Cell-Free Membrane Patches", Hamill et al Pflugers Archiv V391 pp 85–100 (1981). These references are to be incorporated herein in toto for providing a method for identifying sodium channel blockers useful in accordance with the present invention.

EXAMPLE

FIG. 1 shows a representation of a retinal ganglion cell 10, under normal conditions and assumed relevant transport mechanisms 12, 14, 16, 18 responsible for maintaining the sodium (Na+), potassium ($K^+$) and calcium ($Ca^{2+}$) gradients and electrical activity of the cell. As shown under normal conditions ATP levels are adequate and furnish the fuel needed to drive the $Na^+/K^+$ pump 14 that maintains the $K^+$ and $Na^+$ gradients, keeping intracellular concentrations of $K^+$ high and $Na^+$ low relative to their respective extracellular concentrations. The voltage-gated $N^+$ and $K^+$ channels 12, 16 provide the currents that make up the action potential. The electrogenic $Na^+/Ca^{2+}$ exchanger 18 keeps cellular $Ca^{2+}$ levels within the physiological range (nanomolar).

Figure 2:
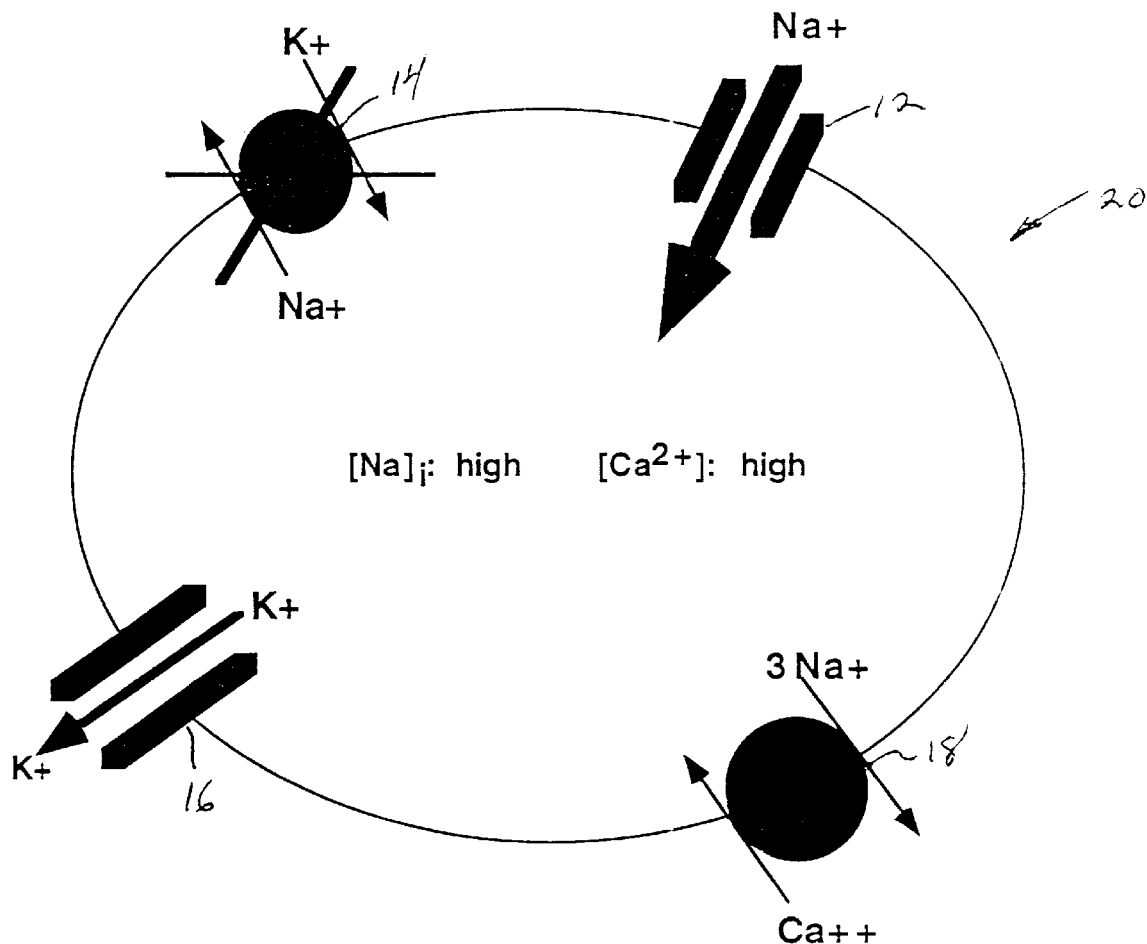
FIG. 2 is a diagram of a retinal ganglion cell under ischemic conditions.

If, however, ATP levels should drop, due to some pathophysiological insult, the axon will depolarize and the $Na^+/K^+$ gradients will collapse over time as a result of $Na^+/K^+$ pump 14 inhibition as shown in FIG. 2 for a cell 20 under ischemic conditions. The rise in cellular $Na^+$ is mediated by a subset of voltage-gated $N^+$ channels are that do not inactivate over time. These $N^+$ channels are coined "noninactivating". The combination of membrane depolarization and intracellular $N^+$ increase is sufficient to drive the $Na^+/Ca^{2+}$ exchanger 18 backwards (see FIG. 2) such that the ganglion cells load with lethal levels of $Ca^{2+}$. It is assumed that this scenario occurs in the retinal ganglion cell in glaucoma.

Accordingly, in accordance with the present invention the following sequence is expected in the presence of a therapeutic concentration of a $Na^+$ channel blocker selective for the noninactivating type. First, the $Na^+$ channel blocker would have little or no effect on the normal action potential. This is crucial for normal ganglion cell function. Second, it will block the deleterious increase in cell $Na^+$ and the subsequent lethal increase in cell $Ca^{2+}$. Thus, normal ganglion cell dysfunction will be minimized and therefore help prevent the loss of visual field associated with glaucoma. In addition, blockers of noninactivating $Na^+$ channels may yield an additional benefit. This is because $N^+$ channels are thought to help prevent excitotoxic glutamate release which occurs in neuronal tissue during ischemia, hypoxia and other pathological conditions. Excessive extracellular glutamate levels are neurodestructive and thus may also be involved in glaucomatous optic neuropathy. Thus, $Na^+$ overload and excitotoxic increase in extracellular glutamate in accordance with the present invention may be prevented by a therapeutic concentration of one drug, a blocker of noninactivating Na$^+$ channels.

In view of the above, it is clear that the scope of the present invention should be interpreted solely on the basis of the following claims, as such claims are read in light of the disclosure.

What is claimed is:

1. A method for preventing retinal ganglion cell death, associated with glaucoma, in an animal of the mammalian species, including humans, comprising the step of administering to the ganglion optic nerve of said mammal a pharmaceutical composition which comprises as its active ingredient one or more compounds having non-inactivating sodium channel blocking activity.

2. The method of claim 1 wherein the compound having non-inactivating sodium channel blocking activity is selected from the group consisting of benzothialzole riluzole, phenyl benzothiozole and lifarizine.

3. The method of treatment of claim 2 wherein the composition is an ophthalmic solution adapted for administration to the eye of a mammal in the form of intracameral injection.

4. The method of treatment of claim 1 wherein in the ophthalmic composition the concentration of the compound having non-inactivating sodium channel blocking activity is in the range of approximately 0.0001 to 1 percent weight by volume.

* * * * *